United States Patent [19]
Kenealy et al.

[11] Patent Number: 5,837,280
[45] Date of Patent: *Nov. 17, 1998

[54] TRANSDERMAL ADMINISTRATION OF AZAPIRONES

[75] Inventors: James N. Kenealy, Miami; Cheryl M. Gentile, Plantation, both of Fla.

[73] Assignee: Sano Corporation, Miramar, Fla.

[ * ] Notice: The term of this patent shall not extend beyond the expiration date of Pat. No. 5,633,009.

[21] Appl. No.: 473,518

[22] Filed: Jun. 7, 1995

Related U.S. Application Data

[63] Continuation of Ser. No. 152,258, Nov. 12, 1993, Pat. No. 5,633,009, which is a continuation of Ser. No. 919,603, Jul. 24, 1992, abandoned, which is a continuation-in-part of Ser. No. 841,869, Feb. 26, 1992, abandoned, which is a continuation of Ser. No. 620,064, Nov. 28, 1990, abandoned.

[51] Int. Cl.$^6$ ................................................. A61F 13/00
[52] U.S. Cl. ........................... 424/449; 424/448; 514/252
[58] Field of Search ................................. 424/448, 449; 514/752

[56] References Cited

U.S. PATENT DOCUMENTS

| | | | |
|---|---|---|---|
| 3,598,122 | 8/1971 | Zaffaroni | 424/435 |
| 3,598,123 | 8/1971 | Zaffaroni | 135/94 |
| 3,717,634 | 2/1973 | Wu et al. | 544/230 |
| 3,731,683 | 5/1973 | Zaffaroni | 424/435 |
| 3,742,951 | 7/1973 | Zaffaroni | 424/434 |
| 3,797,494 | 3/1974 | Zaffaroni | 424/434 |
| 3,976,776 | 8/1976 | Wu | 424/251 |
| 3,996,934 | 12/1976 | Zaffaroni | 424/434 |
| 4,182,763 | 1/1980 | Casten et al. | 514/252 |
| 4,438,119 | 3/1984 | Allen et al. | 514/252 |
| 4,634,703 | 1/1987 | Kurtz et al. | 514/252 |
| 4,640,921 | 2/1987 | Othmer et al. | 514/252 |
| 4,687,772 | 8/1987 | Alderdice | 514/273 |
| 4,705,796 | 11/1987 | Hendry et al. | 514/328 |
| 4,777,173 | 10/1988 | Shrotryia et al. | 514/252 |

(List continued on next page.)

FOREIGN PATENT DOCUMENTS

| | | |
|---|---|---|
| 0 314 984 A2 | 5/1989 | European Pat. Off. . |
| 0 341 202 A1 | 11/1989 | European Pat. Off. . |
| 0431519 | 12/1989 | European Pat. Off. . |
| 0 356 997 A2 | 3/1990 | European Pat. Off. . |
| 0 431 519 A1 | 12/1991 | European Pat. Off. . |
| 0 497 314 A1 | 8/1992 | European Pat. Off. . |
| 56-138113 | 10/1981 | Japan . |
| 58046015 | 3/1991 | Japan . |
| 2 222 768 | 3/1990 | United Kingdom . |
| 91/08795 | 6/1991 | WIPO . |

OTHER PUBLICATIONS

Gawin, et al., "Buspirone Reduces Smoking," *Arch. Gen. Psychiatry*, vol. 46, pp. 288–289 (1989).

Gawin, et al., "Potential Use of Buspirone as Treatment for Smoking Cessation: A Preliminary Trial," *Family Practice Recerification*, vol. 11, No. 9, pp. 74–78 (1989).

Wei, et al., "Effect of Clonidine on Cigarette Cessation and in the Alleviation of Withdrawl Symptoms," *British Journal of Addiction*, vol. 83, pp. 1221–1226 (1988).

New, "The Discovery and Development of Buspirone: A New Approach to the Treatment of Anxiety," *Medicinial Research Reviews*, vol. 10, pp. 183–326 (1990).

Cleary, "Transdermal Drug Delivery," *Cosmetics and Toiletries*, vol. 106, pp. 97–109 (1991).

(List continued on next page.)

*Primary Examiner*—D. Gabrielle Phelan
*Attorney, Agent, or Firm*—Jones & Askew, LLP

[57] ABSTRACT

In accordance with the present invention, a method and device is provided for administering therapeutically effective doses of the drug azospirone transdermally for treating psychogenic symptomatologies. One embodiment of the present invention comprises an effective amount of solubilized azospirone in a transdermal drug delivery device. By practicing the present invention, constant blood concentrations of azospirone can be maintained over a prolonged period of time, side effects can be minimized with maximal patient compliance.

10 Claims, 2 Drawing Sheets

U.S. PATENT DOCUMENTS

| | | | |
|---|---|---|---|
| 4,788,064 | 11/1988 | Patel et al. | 424/449 |
| 4,788,189 | 11/1988 | Glazer | 514/221 |
| 4,839,174 | 6/1989 | Baker et al. | 424/447 |
| 4,871,738 | 10/1989 | Optiz et al. | 514/252 |
| 4,940,585 | 7/1990 | Hapworth | 424/464 |
| 4,943,428 | 7/1990 | Lucot et al. | 514/657 |
| 4,954,343 | 9/1990 | Hosaka et al. | 424/448 |
| 4,963,361 | 10/1990 | Kawazi | 424/443 |
| 4,971,799 | 11/1990 | Nakagawa et al. | 424/448 |
| 4,978,532 | 12/1990 | El-Rashidy | 424/448 |
| 5,032,403 | 7/1991 | Sinnreich | 424/448 |
| 5,185,329 | 2/1993 | Gawin et al. | 514/159 |

OTHER PUBLICATIONS

Eison et al., "Mechanism of Action of Buspirone: Current Perspectives," *Burpirone Mechanisms and Clinical Aspects,* G. Tunnicliff, A. Eison, D. Taylor, eds., Academic Press, Inc., New York, pp. 279–326 (1991).

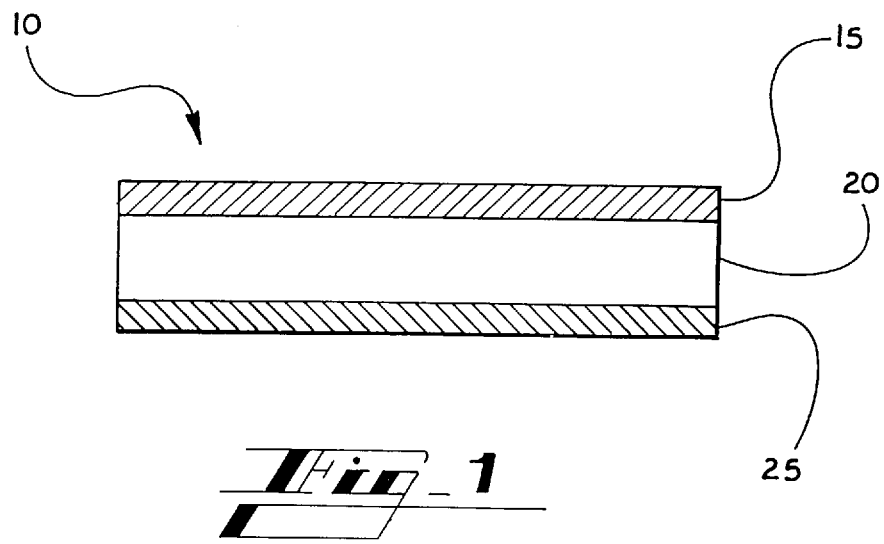
Fig_1
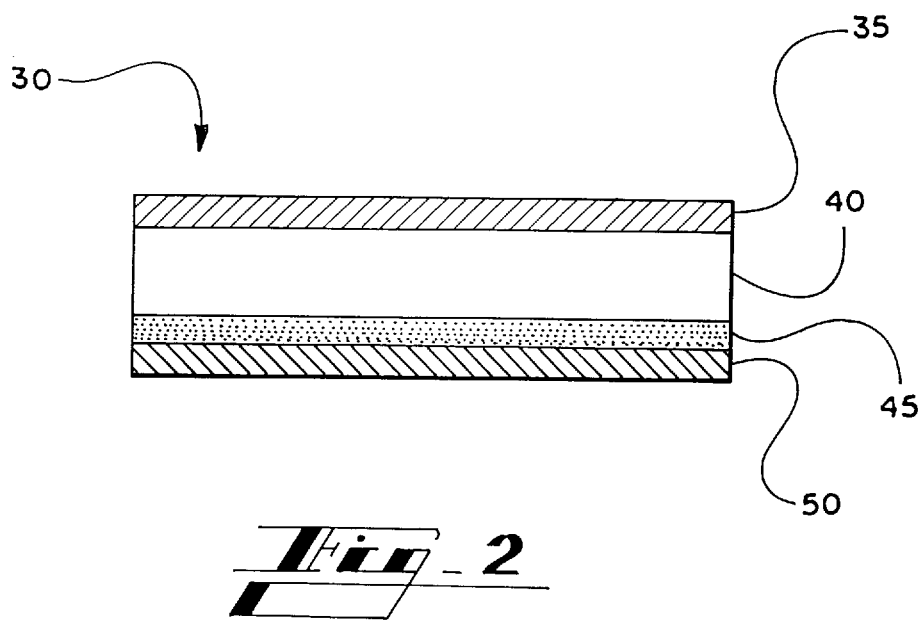
Fig_2

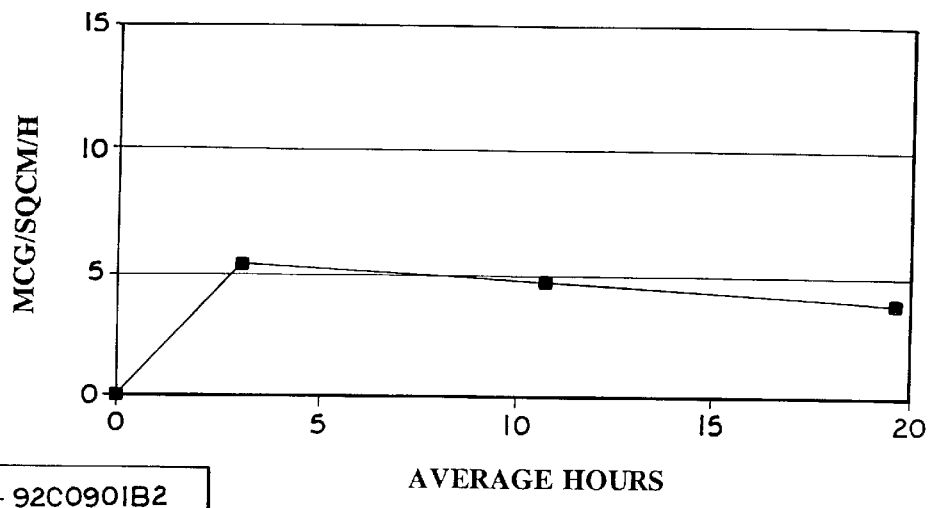
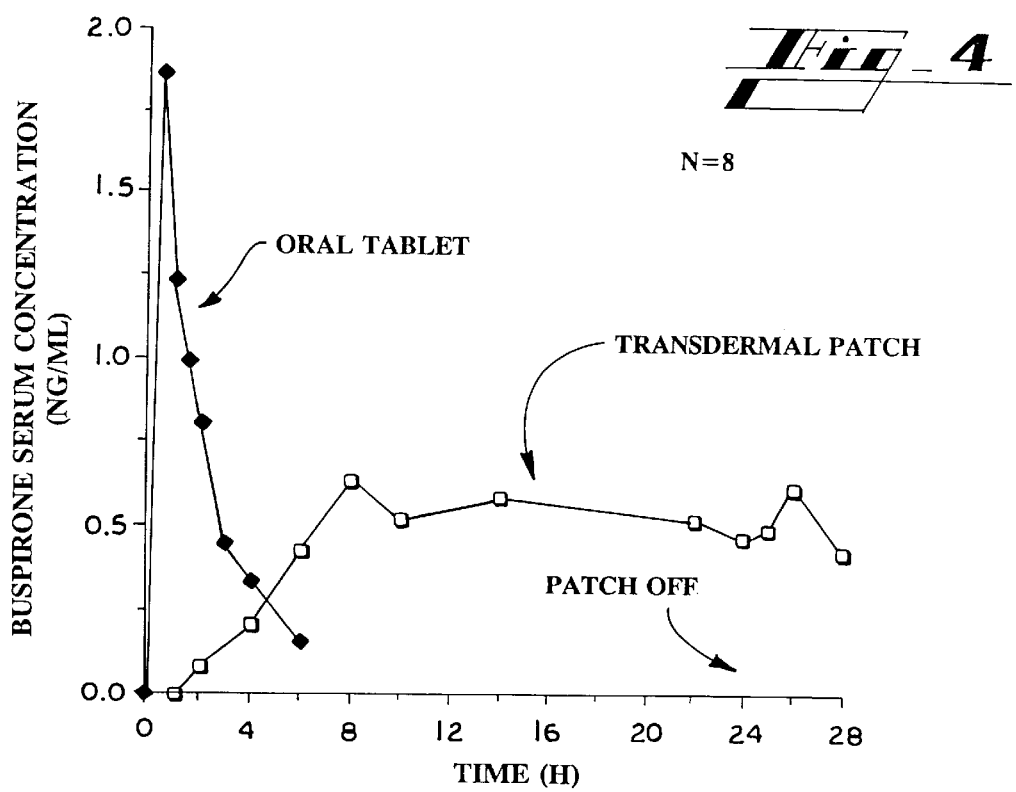

TRANSDERMAL ADMINISTRATION OF AZAPIRONES

CROSS REFERENCE TO RELATED APPLICATIONS

This application is a continuation of U.S. patent application Ser. No. 08/152,258, filed Nov. 12, 1993, which is a continuation of U.S. patent application Ser. No. 07/919,603, filed Jul. 24, 1992, now abandoned, which is a continuation-in-part of U.S. patent application Ser. No. 07/841,869, filed Feb. 26, 1992, now abandoned, which is a continuation of U.S. patent application Ser. No. 07/620,064, filed Nov. 28, 1990, now abandoned.

TECHNICAL FIELD

The present invention relates to the transdermal delivery of azapirones. More particularly the present invention relates to methods and devices for the transdermal delivery of the azapirones including buspirone to treat a variety of psychogenic symptomatologies.

BACKGROUND OF THE INVENTION

"Azaspirone" as used herein means a class of polycyclic amine derivatives including, among others, the following azapirones:

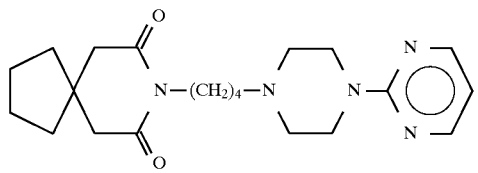

Buspirone, hereinafter;

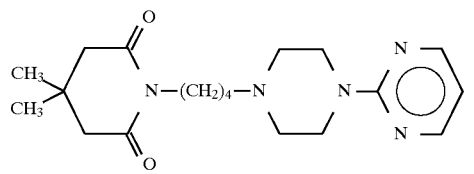

Gepirone, hereinafter;

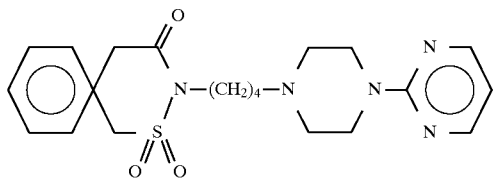

Ipsapirone, hereinafter;

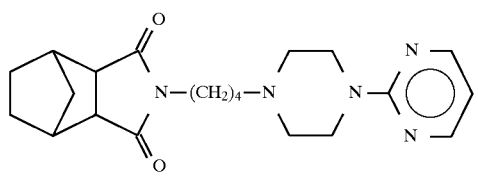

Tandospirone, hereinafter;

-continued

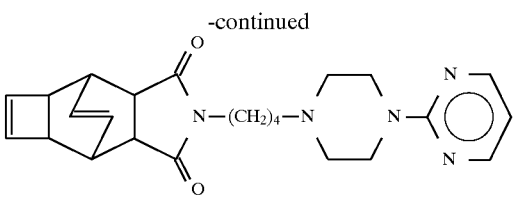

WY-47,846, hereinafter;

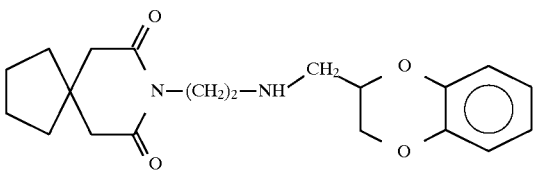

MDL 73005 EF, hereinafter; and

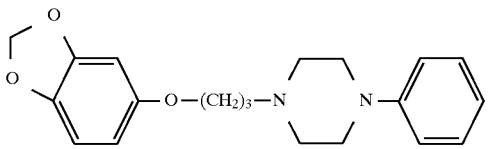

BP-554, hereinafter, other 2-pyrimidinyl-1-piperazine derivatives and piperazinylbutylindole derivatives. "Psychogenic symptomatology" as used herein includes, but is not limited to, anxiety, depression, panic disorders, extrapyramidal motor disorders, loss of short term memory, agitation, sexual dysfunction, obsessive-compulsive disorder, anorexia nervosa, premenstrual syndrome, schizophrenia, childhood autism, respiratory stimulation, phencyclidine abuse, nausea and vomiting and the behavior associated with alcohol abuse, drug addiction and nicotine dependence. "Recrystallization" as used herein means the formation of perceptible to visible crystals. "Solubilized" as used herein means the azospirone dissolved in the transdermal delivery system does not recrystallize over time.

Azapirones have been shown to be effective for treating a variety of psychogenic symptomatologies. It has been reported that the azapirones act on 5- hydroxytryptaminergic neurons. It is proposed that azapirones act by a general inhibition of serotenergic neurotransmission mediated through activation of 5-hydroxytryptamine$_{1A}$ receptors of 5-hydroxytryptaminergic neurons. (See New, J. S., "The discovery and development of buspirone: A new approach to the treatment of anxiety", *Medicinal Research Reviews* 10 (3): 283–326, 1990) azapirones are effective at low systemic blood concentrations, cause no sedation, and have no known abuse potential. Orally administered azapirones, however, produce irregular blood concentrations and depend on patient compliance for their effectiveness. Therefore, what is needed is a transdermal delivery device that maintains a useful flux of azapirone from the transdermal delivery device for a prolonged period. Such a transdermal delivery devise should enable predictable blood concentrations of azapirone and should rely only minimally on patient compliance to maintain this blood concentration.

The best known of the azapirones, is buspirone. Buspirone is effective in reducing nicotine dependence and in the treatment of, among others, anxiety, depression, panic disorders, extrapyramidal motor disorders, loss of short term memory, agitation, sexual dysfunction, obsessive-compulsive disorder, anorexia nervosa, premenstrual syndrome, schizophrenia, childhood autism, respiratory stimulation, phencyclidine abuse, nausea and vomiting and the behavior associated with alcohol abuse and drug addiction. Each of these psychogenic symptomatologies has been shown clinically to be responsive to oral buspirone. However, orally administered buspirone, is poorly absorbed from the gastrointestinal tract with only 1% to 3% of the oral dose reaching the systemic circulation. In addition, oral buspirone produces irregular blood concentrations and it depends on patient compliance for its effectiveness.

Delivery of certain drugs transdermally has been known to be theoretically possible for many years. Transdermal drug delivery devices are generally laminated composites that include a pressure-sensitive adhesive layer which contains the drug and by which the device is attached to the skin and a backing layer which forms the outer surface of the device and which is impermeable to the drug. To date, only limited commercial exploitation of transdermal drug delivery systems has been achieved, because of the many practical problems to be overcome with real systems. These problems include the solubility of the drug in the adhesive layer, the effect of the drug on the adhesive layer and delivery of the drug to the skin and through the stratum corneum and viable epidermis into the systemic circulation at a constant rate over a prolonged period. In addition, transdermal drug delivery devices should maintain their integrity during long-term storage prior to use.

These problems are particularly difficult to overcome in developing a system for the transdermal delivery of azospirones. First, azapirones are crystalline compounds which should be dissolved before incorporation into the transdermal delivery device. The agents used in the transdermal device not only should dissolve the azapirone, but also should solubilize the dissolved azapirone in the delivery device without compromising the potency of the azapirone. Although azapirones do dissolve in a variety of agents, many of these agents do not solubilize the dissolved azapirone in the adhesive layer. Second, the solubilized azapirone should be compatible with the adhesive layer so it does not effect adversely its adhesive properties. Third, the azapirone should remain solubilized in the delivery device throughout its shelf-life. Fourth, when the transdermal azapirone delivery device is applied to the skin, it should release the azapirone at an effective, steady dose so the flux of solubilized azapirone from the delivery device to the skin and then through the stratum corneum and viable epidermis into the systemic circulation. This flux should be maintained for relatively long periods of time.

Exploitation of the transdermal administration route of azapirones has not been achieved because, although azapirones dissolve in a variety of agents, they have a tendency to recrystallize. Therefore, it is a matter of real difficulty and, to applicants' knowledge, a previously unsolved problem, to find dissolving agents that can solubilize sufficient amounts of azapirones, that do not adversely effect the adhesive layer and that can release the solubilized azapirones in a controlled fashion over a prolonged period.

What is needed is a method of administering buspirone and other azapirones that allows for predictable blood concentrations of the drug for a prolonged period and that relies only minimally on patient compliance.

SUMMARY OF THE INVENTION

The present invention comprises the transdermal delivery of compounds that are a member of the class of compounds known collectively as azapirones. These compounds include buspirone and salts of buspirone. It has been found that buspirone can be delivered transdermally in amounts which are therapeutically effective.

The present invention provides in one embodiment a transdermal delivery device, comprising a pressure-sensitive adhesive layer containing a sufficient quantity of solubilized azapirone to maintain an effective flux of azapirone from the transdermal delivery device for a prolonged period and a backing layer substantially impermeable to the solubilized azapirone. The present invention also provides a method for treating psychogenic symptomatology in a warm blooded animal in need of such treatment by the percutaneous administration of azapirone for a prolonged period.

The azapirones are administered via a transdermal delivery device which can be, among others, a three-layer laminate comprising a backing layer, a pressure-sensitive adhesive layer containing solubilized azapirone and a release liner layer or, in another embodiment, a four-layer laminate comprising a backing layer a solubilized azapirone loaded matrix layer, a pressure-sensitive adhesive layer and a release liner layer.

The present invention is designed to deliver an azapirone over a prolonged period at an approximately constant rate. For example, in one embodiment, the patient only has to apply or have applied the transdermal delivery device with the solubilized azapirone therein once each 24 hour period to maintain an approximately constant blood concentration of azapirone over this time period. Another advantage of the present invention is the minimal patient compliance required as the transdermal patch must be applied only once every 24 or more hours. Because the azapirone blood concentration remains relatively constant by using the present invention, the success of treating psychogenic symptomatology effectively in a patient in need of such treatment is increased over that of prior art methods.

Accordingly, it is an object of the present invention to provide a transdermal delivery device for the percutaneous delivery of azapirones.

It is yet another object of the present invention to provide a method for treating psychogenic symptomatology in a patient in need of such treatment.

It is another object of the present invention to provide a method for treating the symptoms associated with nicotine dependence.

It is another object of the present invention to provide a method to reduce the symptoms associated with withdrawal from tobacco.

It is another object of the present invention to provide a method for reducing anxiety.

It is yet another object of the present invention to provide a method for reducing nausea and vomiting.

It is another object of the present invention to provide a method for reducing alcohol consumption and dependence.

It is another object of the present invention to provide a method for reducing drug consumption and dependence.

It is another object of the present invention to provide a method which improves short term memory.

It is another object of the present invention to provide a method for treating panic disorders.

It is another object of the present invention to provide a method for reducing premenstrual syndrome.

It is another object of the present invention to provide a method for treating sexual dysfunction.

It is another object of the present invention to provide a method for treating depression.

It is another object of the present invention to provide a method for treating anorexia nervosa.

It is another object of the present invention to provide a method for treating anxiety neuroses.

It is another object of the present invention to provide a method for treating extrapyramidal motor disorders.

It is another object of the present invention to provide a method for treating aggression.

It is another object of the present invention to provide a method for treating childhood autism.

It is another object of the present invention to provide a method for treating dyspnea.

It is another object of the present invention to provide the azapirones or their derivatives and metabolites in a transdermal delivery device.

It is another object of the present invention to solubilize the azapirones in the pressure-sensitive adhesive layer of a transdermal delivery device.

It is another object of the present invention to provide a transdermal delivery device capable of sustained controlled release of azapirones over a prolonged period.

It is another object of the present invention that the transdermal delivery device not require a discrete membrane layer for control of the azapirone flux.

It is another object of the present invention to maintain concentrations of azapirones in the systemic circulation sufficient to treat psychogenic symptomatology in a patient in need of such treatment for prolonged periods.

It is another object of the present invention to provide buspirone or its derivatives and metabolites with a transdermal delivery service.

It is another object of the present invention to provide a transdermal delivery device capable of sustained controlled release of buspirone over a prolonged period.

These and other objects, features and advantages of the present invention will become apparent after a review of the following detailed description of the disclosed embodiment and the appended claims.

BRIEF DESCRIPTION OF THE FIGURES

FIG. 1 is a cross-sectional view of the transdermal azapirone delivery system.

FIG. 2 is a cross-sectional view of another embodiment of the transdermal azapirone delivery system.

FIG. 3 is a graph of the flux across human cadaver skin of buspirone released from a polyisobutylene pressure-sensitive adhesive matrix loaded with 1.5% by weight of buspirone solubilized with 12.5% by weight of isocetyl alcohol.

FIG. 4 is a graph comparing buspirone serum concentration levels in eight healthy, adult male volunteers using the transdermal delivery system of this invention and using oral buspirone tablets.

DETAILED DESCRIPTION OF THE PRESENT INVENTION

The present invention comprises the transdermal delivery of azapirones and more particularly of buspirone. The present invention includes all forms of transdermal delivery of azapirones including, but not limited to, transdermal devices such as devices in liquid form with a fill and seal laminate structure, peripheral adhesive laminate structures and solid state adhesive laminate structure or with the drug in the adhesive. Transdermal drug delivery is discussed in general in Cleary, G. W., "Transdermal Drug Delivery", *Cosmetics & Toiletries,* Vol. 106, pgs. 97–109, 1991 which is incorporated herein by reference.

The present invention provides a transdermal drug delivery system comprising a pressure-sensitive adhesive layer containing a sufficient amount of solubilized azapirone to maintain an effective flux of the azapirone for a prolonged period and a backing layer substantially impermeable to the solubilized azapirone. The present invention also provides a method for treating psychogenic symptomatology in a patient in need of such treatment. The method comprises the step of applying to the skin of the individual a transdermal delivery device, the transdermal delivery device comprising a pressure-sensitive adhesive layer containing a sufficient quantity of solubilized azapirone to deliver through the skin between approximately 0.2 $\mu g/cm^2/hr$ and 100 $\mu g/cm^2/hr$ of azapirone based on a patch size of 1 to 200 $cm^2$. A more preferred flux rate is between approximately 0.5 $\mu g/cm^2/hr$ and 50 $\mu g/cm^2/hr$ of an azapirone such as buspirone based on a patch size of between approximately 2 to 60 $cm^2$.

It is to be understood that the present invention includes the transdermal administration of compounds that belong to the class of compounds known generally as azapirones. It is contemplated that the transdermal administration can be accomplished by any of the transdermal devices known to those of ordinary skill in the art. The embodiments disclosed herein are only meant to be examples of the transdermal administration of azapirones.

As illustrated in FIG. 1, the transdermal delivery device of one embodiment of the invention has an impermeable backing layer 15, a solubilized azapirone loaded pressure-sensitive adhesive layer 20, and a release liner layer 25, impermeable to constituents of the pressure-sensitive adhesive layer.

As illustrated in FIG. 2, the transdermal delivery system 30 of a second embodiment of the present invention has an impermeable backing layer 35, a solubilized azapirone loaded matrix layer 40, a pressure-sensitive adhesive layer 45, and a release liner layer 50 impermeable to the constituents of the matrix layer 40 and of the pressure-sensitive adhesive layer 50.

The virtually impermeable backing layer 15 and 35 defines the first face of the transdermal delivery device or the side furthermost away from the skin. The impermeable backing layer 15 and 35 protects the transdermal delivery device and prevents the escape of constituents of the pressure-sensitive adhesive layer 20 or of the matrix layer 40 and the pressure-sensitive adhesive layer 45 into the environment.

Material used for the backing layer 15 and 35 of each embodiment should be impermeable to solubilized azapirone. The backing layer material should form a support to hold the pressure-sensitive adhesive layer 20 or the matrix layer 40 and the pressure-sensitive adhesive layer 45 in comfortable contact with the patient's skin. Suitable materials for use in the backing material include, but are not limited to, dermatologically acceptable films such as polyesters, polyurethanes, polyolefins, rubbers, synthetic resins, cloth, foils, and various laminates of these materials.

The azapirone loaded pressure-sensitive adhesive layer 20 and the azapirone loaded matrix layer 40 each contain a solubilizing agent or combination of agents which dissolve the azapirone and which solubilize the azapirone in the pressure-sensitive adhesive layer 20 and in the matrix layer 40.

The common agents in which azapirones dissolve readily include, but are not limited to, benzyl alcohol, transcutol, dimethyl isosorbide and fatty acids. However, many of these agents do not adequately solubilize azapirones in the pressure-sensitive adhesive layer or in the matrix layer and the dissolved compound has been found to recrystallize with time. In addition, many of the fatty acids normally used in the prior art adversely effect the properties of pressure-sensitive adhesives.

The solubilization agents in which azapirones dissolve, include, but are not limited to, fatty acids, fatty alcohols, fatty esters, fatty ethers, glycerides, surfactants, oils, alcohols and diol groups. Fatty acids include soya fatty acid, linoleic acid, oleic acid, lauric acid, myristic acid, and palmitic acid. Fatty alcohols include oleyl alcohol and isocetyl alcohol. Fatty esters include isostearyl isostearate, cetearyl isononanoate, 2 octyl dodecyl myristate, isopropyl myristate, coco caprylate/caprate, glycol ester, isocetyl stearate, and hexyl laurate. Oleates include polyetheneglycol oleate, oleyl oleate, decyl oleate, and polyoxyethylene glycol oleate. Fatty ethers that can be used as a solubilization agent in the present invention include cetyl ether and oleyl ether. Glycerides include triesters of capric/capric acids, caprylic/capric monoglycerides, caprylic/capric glycerides and adipic/isostearic triglyceride. Glycols include polyethylene glycols, butylene glycol, dipropylene glycol, and propylene glycol. Oils and lipids include maleated soybean oil and lecithin derivatives. It is to be understood that the above list of solubilization agents is only representative of the compounds that can be used in practicing the present invention and is not meant to be an exhaustive or exclusive list of solubilization agents. One compound, isocetyl alcohol, is a preferred solubilization agent. Isocetyl alcohol unexpectedly solubilized the azapirone buspirone in the pressure-sensitive adhesive layer and, even at relatively high concentrations, did not destroy the adhesive layer. The preferred range of solubilizing agents for use in this invention is between approximately 0.1% to 75%. A more preferred range is between approximately 2% and 40%. A most preferred range is between approximately 5% and 25%.

In one embodiment of this invention 10, solubilized or partially solubilized azapirone, such as buspirone, is dispersed in pressure-sensitive adhesives. Material used in the pressure-sensitive adhesives include, but are not limited to, natural rubber, styrene-butadiene-rubber polymers, styrene-butadiene-styrene or styrene-isoprene-styrene block copolymers, polyisoprene, polyisobutylene, butyl rubber, polyacrylates, silicone pressure-sensitive adhesives, and vinyl ether polymers. The addition of tackifiers, plasticizers, fillers, pigments, antioxidants and unsaturated resins, partially saturated resins and fully saturated resins may be necessary to obtain desirable adhesive properties. Preferred pressure-sensitive adhesives include polyisobutylene available from the Exxon Chemical Company, Houston, Tex., and polyisobutylene plus a tackifier resin. Tackifier resins may be broken into two major groups: the rosin group and the hydrocarbon resin group. Rosin, by itself, is generally unsuitable for adhesive use because of oxidation. Therefore, most rosins are modified rosins or rosin derivatives. Hydrocarbon tackifier resins are low molecular weight polymers derived from crude monomer streams. Preferred tackifier resins include hydrogenated hydrocarbon, phenol-formaldehyde, rosin ester, terpene, and terpene-phenolic resins. The most preferred tackifier resins are the hydrogenated hydrocarbon resins such as Escorez 5300, 5320 and 5380 available from Exxon Chemical Company, Houston, Tex. The preferred range of pressure-sensitive adhesive for use in this invention is between approximately 5% and 99.8%. A more preferred range is between approximately 30% and 95%. A most preferred range is between approximately 60% and 90%. The amount of tackifier resin to be added to the preferred range of pressure-sensitive adhesive is known to those of ordinary skill in the art.

The transdermal delivery device of the present invention may be assembled by any of the techniques known in the art. For example, the pressure-sensitive adhesive layer may be cast onto the backing layer, onto the release liner (peel strip) layer or onto an intermediary support film.

The invention may include a release liner (peel strip). The release liner (peel strip) layer 25 covers the surface of the pressure-sensitive adhesive during storage, protects the pressure-sensitive adhesive layer and helps maintain drug stability. The release liner (peel strip) layer may be made from any impermeable film including, but not limited to, that specified for the backing layer. One preferred class of materials for use in the release liner (peel strip) layer is polyester.

An azapirone which has been used clinically is buspirone. Buspirone is described in U.S. Pat. No. 3,717,634, which is incorporated herein by reference. It is to be understood that the term "buspirone" means any chemical disclosed by U.S. Pat. No. 3,717,634 and therapeutically effective metabolites thereof. Other acid addition salts thereof can be named by combining, for example, buspirone with the appropriate word to define the acid from which it is prepared as in "buspirone hydrochloride." The term "buspirone" includes all salts of the base compound. The azapirone "buspirone" has the following formula:

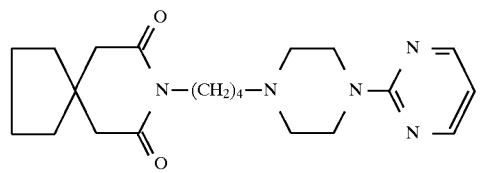

Other azapirones include, but are not limited to, gepirone, ipsapirone, tandospirone, WY-47,846, SM-3997, MDL-73005 RF, BP-554, other 2-pyrimidinyl-1-piperazine derivatives, piperazinylbutylindole derivatives, and other polycyclic amine derivatives. The preferred range of azapirone for use in the present invention is between approximately 0.1 to 50%. A more preferred range is between approximately 0.25% to 25%. A most preferred range is between approximately 0.5% and 5%.

The amount of drug to be incorporated in a transdermal azapirone delivery device will vary depending on the dosage desired, the permeability of the pressure-sensitive adhesive materials, the thickness of the pressure-sensitive adhesive layer, and the length of time the transdermal delivery device is to remain on the skin and other factors which are known to those skilled in this art. To achieve a therapeutic effect, the buspirone flux from the transdermal delivery device through skin should be in the range between 0.004 mg and 2.5 mg per hour. Thus, for example, an acceptable transdermal delivery device will deliver a maximum of approximately 60 mg of buspirone per 24 hours and a minimum of approximately 0.1 mg of buspirone per 24 hours. These rates may vary depending upon the symptom being treated.

A second embodiment of the transdermal delivery device 30, shown in FIG. 2, comprises a backing 35 and release liner 50, a buspirone containing matrix layer 40, and an adhesive layer 45. The buspirone matrix layer 40 comprises solubilized or partially solubilized buspirone dispersed in a matrix. Suitable matrix materials include, but are not limited to, polysaccharides such as starch, cellulose, hyaluronic acid, pectin, seaweed gums and vegetable gums; polypeptides such as casein, albumin, keratin and collagen; thermoplastics such as unvulcanized elastomers, nylon, polyethylene (linear), polyurethane, acrylic resins, cellulose resins, and polypropylene; polyethylene glycols; polyvinylacetates; polyvinyl alcohols; and polyvinylpyrrolidones. For polyurethanes the polyether type is preferred, because in general it is more inert than polyester types, and thus more appropriate for medical use. Polymers of this type are available from B. F. Goodrich Company, Brecksville, Ohio. The non-adhesive matrix layer of the transdermal drug delivery device of the present invention can have between approximately 20% to 99.8% non-adhesive matrices and between approximately 0.1% and 50% buspirone and between approximately 0.1% and 75% solubilizing agents.

The pressure-sensitive adhesive layer 45 contains a dermatologically acceptable adhesive or adhesives. A suitable adhesive is polyisobutylene or double sided adhesive.

To prepare a transdermal buspirone delivery device, the buspirone or other azapirone compound is dissolved or dispersed in the solubilizing agent or agents and pressure-sensitive adhesive or polymer matrix. The percentage of solubilized buspirone in the pressure-sensitive adhesive or in the polymer matrix may be varied according to the desired loading of the finished pressure-sensitive adhesive layer or polymer matrix layer The preferred range of buspirone for use in the present invention is between approximately 0.1% to 50%. A more preferred range is between approximately 0.25% to 25%. A most preferred range is between approximately 0.5% and 5%. The preferred range of solubilizing agents for use in this invention is between approximately 0.1% to 75%. A more preferred range is between approximately 2% and 40%. A most preferred range is between approximately 5% and 25%. The ratio of buspirone to solubilizing agent or agents may vary between approximately 1:0.02 and 1:200, more preferably between approximately 1:1 and 1:40 and most preferably between approximately 1:5 and 1:20. For example, where it is desired to release between approximately 0.1 mg and approximately 60 mg of buspirone in a 24 hour period, the preferred solubilized buspirone load in the pressure-sensitive adhesive or in the non-adhesive matrix is between approximately 0.1% and 50%.

The pressure-sensitive adhesive or polymer matrix layer may be processed by utilizing the art known in casting (pouring into a mold or on a moving flat surface), coating, extrusion, hot melt applications, radiation curing or other methods known in the art. The matrix will typically have a thickness in the range of 10 to 6400 microns. For a given total buspirone load, loading may be varied by varying the matrix thickness.

The pressure-sensitive adhesive or polymer matrix layer is then laminated to the backing layer and to the release liner (peel strip) layer by techniques known in the art, to form the multilayered structures shown in FIGS. 1 and 2. Patches of the desired size are punched or cut from the laminate by techniques known in the art. Punched patches can range from approximately 1 to 200 $cm^2$. The more preferable patch size is from 2 to 60 $cm^2$. The size of the patch will vary according to the amount of buspirone to be delivered over a 24 hour period. To prevent contamination and to maintain the stability of the buspirone and the adhesive, the punched transdermal buspirone delivery devices are preferably sealed in individual pouches or other suitable materials until used. It should be noted that the transdermal patch which is contemplated as the present invention can be used anywhere on the body where the patch can be applied to the skin.

This invention is further illustrated by the following examples, which are not construed in any way as imposing limitations upon the scope thereof. On the contrary, it is to be clearly understood that resort may be had to various embodiments, modifications, and equivalents thereof which, after reading the description herein, may suggest themselves to those skilled in the art without departing from the spirit of the present invention and/or the scope of the appended claims.

EXAMPLE 1

The present invention includes the administration of buspirone in a transdermal delivery device. In one embodiment of a transdermal delivery device according to the present invention, buspirone solution is added to isocetyl alcohol. The buspirone/isocetyl alcohol solution is added to a polyisobutylene solution and the two solutions are blended until the mixture is homogeneous. The mixture is then coated uniformly onto a layer of release coated polyester film and dried at a temperature between approximately 20° C. and 90° C. until the solvents evaporate and the system has pressure-sensitive adhesive properties. The dry weight of the mixture is approximately 10 mg per $cm^2$, and contains 1.5% buspirone, 12.5% isobutyl alcohol, 86% polyisobutylene.

The system is then laminated to a polyester film laminate to form a triple laminate of backing layer/solubilized buspirone loaded pressure-sensitive adhesive layer/release liner (peel strip) layer. The laminate is then punched into units of 10 $cm^2$, containing 0.15 mg/$cm^2$ of buspirone, which are stored in individual packets for use within 24 months.

For use, one transdermal buspirone delivery device is removed from its packet, the release liner (peel strip) layer is removed and discarded, and the solubilized buspirone loaded pressure-sensitive adhesive is applied firmly to the patient's arm. The transdermal buspirone delivery system is left in place for 24 hours.

EXAMPLE 2

In another embodiment, buspirone, 2% by weight is partially solubilized in 15% by weight of isocetyl alcohol. The isocetyl alcohol solubilized buspirone is heated and is added to and mixed with molten polyvinylacetate which has been melted slowly to obtain a working viscosity of 10,000 to 20,000 cps. The matrix layer mixture is slot die coated onto the backing layer. To do this, the mixture is allowed to flow through a slot to form a thin coat of a desired thickness, containing approximately 20 mg/$cm^2$ of the mixture, which is deposited onto a layer of polyester film laminate backing layer (ScotchPak 1012, 3M Corporation, St. Paul, Minn.).

A layer of double-sided pressure-sensitive polyacrylate adhesive and a layer of silicone coated polyester release liner are laminated to the face of the matrix facing away from the backing layer to form a quadruple laminate of backing layer/buspirone loaded matrix layer/pressure-sensitive adhesive layer/release liner (peel strip) layer. The laminate is then punched into transdermal units of 10 $cm^2$, containing 0.4 mg/$cm^2$ of buspirone and stored in individual packets for use within 24 months. After 24 months, examination of the patch reveals no recrystallization of the ipsapirone. For use, one transdermal buspirone delivery device is removed from its packet, the release liner (peel strip) layer is removed and discarded, and the pressure-sensitive adhesive layer is applied firmly to the patient's arm. The transdermal buspirone delivery device is left in place for 24 hours.

EXAMPLE 3

A transdermal delivery device is prepared as outlined in Example 1. A patch 2.5 $cm^2$ is applied to piece of human cadaver skin. This patch delivers buspirone through the human cadaver skin at a rate of approximately 4 μg/cm²/h over a 24 hour delivery period. FIG. 3 shows the flux across the human cadaver skin of buspirone released from the polyisobutylene pressure-sensitive adhesive matrix loaded with 1.5% by weight of buspirone solubilized with 12.5% by weight of isocetyl alcohol.

EXAMPLE 4

A transdermal delivery device is prepared as outlined in Example 1. A patch 40 cm² is applied to piece of human cadaver skin. This patch delivers buspirone through the human cadaver skin at a rate of approximately 4 μg/cm²/h over a 24 hour delivery period.

EXAMPLE 5

A transdermal delivery device is prepared as outlined in Example 1. A first patch of 20 cm² is maintained at room temperature for 6 months. A second patch of 20 cm² is maintained at 40° C. for 6 months. At the end of the six months, the first patch and the second patch are each applied to a piece of human cadaver skin. Both patches deliver buspirone through the human cadaver skin at a rate of approximately 4 μg/cm²/h over a 24 hour delivery period.

EXAMPLE 6

A transdermal delivery patch is prepared so that the dry product, a pressure sensitive adhesive containing 2% buspirone, 25% isocetyl alcohol and 73% polyisobutylene is laminated to a backing material. A patch 2.5 cm² is applied to piece of human cadaver skin. This patch delivers buspirone through the human cadaver skin at a rate of approximately 5 μg/cm²/h over a 24 hour delivery period.

EXAMPLE 7

A transdermal delivery device is prepared as outlined in Example 6. A first patch of 20 cm² is maintained at room temperature for 6 months. A second patch of 20 cm² is maintained at 40° C. for 6 months. At this time, the first patch and the second patch are each applied to a piece of human cadaver skin. Both patches deliver buspirone through the human cadaver skin at a rate of approximately 5 μg/cm²/h over a 24 hour delivery period.

EXAMPLE 8

In another embodiment, 2% by weight of gepirone, 25% by weight of isocetyl alcohol and 63% by weight of polyisobutylene and 10% by dry weight of a hydrogenated hydrocarbon resin such as Escorez 5380 are blended. The blend is coated onto a layer of release coated polyester film and dried so that the dry weight of the blend is approximately 10 mg/cm². The dry product is laminated to a polyester film laminate backing material. A patch 2.5 cm² is applied to piece of human cadaver skin. This patch delivers gepirone through the human cadaver skin at a rate of approximately 5 μg/cm²/h over a 24 hour delivery period.

EXAMPLE 9

Transdermal buspirone delivery devices are prepared as in Example 1. A delivery device of 20 cm² is applied to the skin of 8 healthy, adult male volunteers and is left in place for 24 hours. Blood is collected prior to application of the delivery device and at 1, 2, 4, 6, 8, 10, 14, 22, and 24 hours subsequent to application of the transdermal buspirone delivery device. The amount of buspirone in the serum is determined by gas chromatography. One week later, the same volunteers, after fasting for 12 hours, are given 20 mg of buspirone by mouth. Blood is collected prior to the oral buspirone and at 0.5, 1, 1.5, 2, 3, 4, and 6 hours subsequent to the oral buspirone. The amount of buspirone in the serum is determined by gas chromatography. FIG. 4 illustrates the mean serum buspirone concentration obtained using the transdermal buspirone delivery device and using the oral buspirone. The mean pharmacokinetic parameters for the transdermal buspirone and the oral buspirone are shown in Table I:

TABLE I

| Parameter | Transdermal | Oral |
| --- | --- | --- |
| Area Under the Curve ng.h/ml | 12.73 (19.2)* | 3.71 (66.0) |
| Maximum. Concentration ng/ml | 0.79 (24.0) | 2.17 (91.7) |
| Time to Maximum. h | 16.5 (55.8) | 0.8 (57.5) |

\* = mean (coefficient of variation)

The buspirone transdermal dose corresponds to an approximate oral buspirone dose of 20 mg three times a day or 60 mg per day.

EXAMPLE 10

Transdermal delivery devices are prepared as described in Example 1. A transdermal buspirone delivery device 20 cm² is applied to the skin of each of five individuals who are attempting to stop smoking and who are suffering from nicotine withdrawal symptoms. The buspirone delivery devices are changed once a day for 21 days. At the end of the 21 days, each of the individuals reports a decrease in nicotine dependence and decrease in symptoms including drowsiness, restlessness, headache, irritability, inability to concentrate, and increased appetite.

EXAMPLE 11

Transdermal delivery devices are prepared as described in Example 6. Twenty out-patients comprised of both males and females and suffering from clinically assessed depression are divided into two groups. One group is given transdermal buspirone delivery devices to apply daily for four-weeks. The other group is given transdermal delivery devices containing no buspirone, placebo patches, to be worn daily for four weeks. At the end of the four week treatment period, the patients using the transdermal buspirone delivery devices demonstrate significant improvement over the patients using the transdermal delivery devices without buspirone.

EXAMPLE 12

Transdermal delivery devices are prepared as described in Example 6 These buspirone delivery devices are applied to the skin of eight women suffering from premenstrual syndrome for five days preceding the onset of menstruation. Each patient reports a decrease in her symptoms during the five day period the transdermal buspirone delivery devices are used.

While the invention has been described in detail and with reference to specific embodiments thereof, it will be apparent to one skilled in the art that various changes and modifications can be made therein without departing from the spirit and scope thereof.

We claim:

1. A transdermal composition for use in the administration of an azapirone into the circulation of a warm-blooded animal by absorption through the skin or mucosa of the warm-blooded animal, the composition comprising:
   a. an adhesive layer containing an azapirone and a solubilizing agent effective to inhibit recrystallization of the azapirone within the adhesive layer, the adhesive layer having a first face and a second face, and b. a backing layer substantially impermeable to the azapirone and contacting the first face of the adhesive layer.

2. The composition of claim 1, wherein the azapirone is selected from the group consisting of buspirone, gepirone, ipsapirone, tandospirone, WY-47,846, MDL-73005EF PB-544 and azapirone 13859.

3. The composition of claim 1, wherein the solubilizing agent is selected from the group consisting of a fatty alcohol, a fatty ether, a fatty acid, a fatty ester, a glyceride and a glycol.

4. The composition of claim 3, wherein the solubilizing agent is a fatty alcohol.

5. The composition of claim 4, wherein the fatty alcohol is isocetyl alcohol.

6. A transdermal composition for use in the administration of an azapirone to the circulation of a warm-blooded animal by absorption through the skin or mucosa of the warm-blooded animal, the composition comprising:
   a. a matrix layer containing an azapirone and a solubilizing agent effective to inhibit recrystallization of the azapirone within the matrix layer, the matrix layer having a first face and a second face;
   b. an adhesive layer containing a solubilizing agent effective to inhibit recrystallization of the azapirone within the adhesive layer and contacting the first face of the matrix layer; and
   c. a backing layer substantially impermeable to the azapirone and contacting the second face of the matrix layer.

7. The composition of claim 1, wherein the azapirone is selected from the group consisting of buspirone, gepirone, ipsapirone, tandospirone, WY-47,846, MDL-73005EF, PB-544 and azapirone 13859.

8. The composition of claim 4, wherein the solubilizing agent is selected from the group consisting of a fatty alcohol, a fatty ether, a fatty acid, a fatty ester, a glyceride and a glycol.

9. The composition of claim 8, wherein the solubilizing agent is a fatty alcohol.

10. The composition of claim 9, wherein the fatty alcohol is isocetyl alcohol.

* * * * *